(12) United States Patent
Neubach et al.

(10) Patent No.: US 9,420,995 B2
(45) Date of Patent: *Aug. 23, 2016

(54) ULTRASOUND GUIDED ROBOT FOR FLEXIBLE NEEDLE STEERING

(71) Applicant: Technion Research & Development Foundation Ltd., Haifa (IL)

(72) Inventors: Zipi Neubach, Netanya (IL); Moshe Shoham, Hoshaya (IL)

(73) Assignee: TECHNION RESEARCH & DEVELOPMENT FOUNDATION LTD. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/164,584

(22) Filed: Jan. 27, 2014

(65) Prior Publication Data

US 2014/0142429 A1  May 22, 2014

Related U.S. Application Data

(63) Continuation of application No. 12/994,864, filed as application No. PCT/IL2009/000537 on May 31, 2009, now Pat. No. 8,663,130.

(60) Provisional application No. 61/071,954, filed on May 28, 2008.

(51) Int. Cl.
*A61B 5/103* (2006.01)
*A61B 8/08* (2006.01)

(52) U.S. Cl.
CPC ..................................... *A61B 8/485* (2013.01)

(58) Field of Classification Search
CPC ....................................................... A61B 8/485

USPC ......... 600/407, 437–469, 508, 517, 518, 562, 600/585, 587; 606/130
See application file for complete search history.

(56) References Cited

U.S. PATENT DOCUMENTS 6,558,309 B2 * 5/2003 Hogendijk et al. ................ 600/7
6,676,706 B1 * 1/2004 Mears et al. .................. 623/22.4
(Continued)

FOREIGN PATENT DOCUMENTS

| CN | 101065067 A | 10/2007 |
| CN | 101175444 A | 5/2008 |
| WO | WO2007141754 A3 | 12/2007 |

OTHER PUBLICATIONS

Office Action of the Chinese Patent Office in corresponding Chinese patent application No. 201410637274.1, dated Mar. 2, 2016, and English translation.

*Primary Examiner* — Sanjay Cattungal
(74) *Attorney, Agent, or Firm* — Daniel Feigelson; Fourth Dimension IP (57) ABSTRACT

A robotic system for flexible needle steering under ultrasound imaging. A robot is used to steer the needle along a predetermined curved trajectory by maneuvering the needle base. The needle tip position is detected by an ultrasound sensor and the tracking error of the needle tip from a predetermined needle path is input to a controller which solves the inverse kinematic based on the needle position, and the needle and tissue properties. The control algorithm uses a novel method to detect the elastic properties of the tissue by analyzing tissue motion at the region in front of the needle tip. The inverse kinematic solution may be performed on a model of the needle as a flexible beam having laterally connected virtual springs to simulate lateral forces exerted by the tissue elasticity. The system is able to direct the needle to a target within the tissue while circumventing forbidden regions.

10 Claims, 6 Drawing Sheets

(56) References Cited

U.S. PATENT DOCUMENTS

| | | | |
|---|---|---|---|
| 6,704,694 B1* | 3/2004 | Basdogan et al. | 703/4 |
| 7,102,635 B2* | 9/2006 | Shih et al. | 345/419 |
| 7,217,242 B2* | 5/2007 | Alam et al. | 600/439 |
| 7,225,404 B1* | 5/2007 | Zilles et al. | 715/701 |
| 7,259,761 B2* | 8/2007 | Shih et al. | 345/419 |
| 7,822,458 B2* | 10/2010 | Webster et al. | 600/407 |
| 7,850,456 B2* | 12/2010 | Chosack et al. | 434/272 |
| 7,974,681 B2 | 7/2011 | Wallace et al. | |
| 8,734,349 B2* | 5/2014 | Kruecker et al. | 600/437 |
| 2004/0068188 A1* | 4/2004 | Robinson | 600/447 |
| 2005/0203413 A1* | 9/2005 | Fichtinger et al. | 600/461 |
| 2006/0293643 A1* | 12/2006 | Wallace et al. | 606/1 |
| 2007/0016067 A1* | 1/2007 | Webster et al. | 600/464 |
| 2007/0021738 A1* | 1/2007 | Hasser et al. | 606/1 |
| 2008/0007517 A9* | 1/2008 | Peshkin et al. | 345/156 |
| 2008/0010705 A1* | 1/2008 | Quaid et al. | 901/8 |
| 2009/0036902 A1* | 2/2009 | DiMaio et al. | 606/130 |
| 2009/0149867 A1* | 6/2009 | Glozman et al. | 606/130 |
| 2010/0312129 A1* | 12/2010 | Schecter | 600/508 |

* cited by examiner

ULTRASOUND GUIDED ROBOT FOR FLEXIBLE NEEDLE STEERING

CROSS REFERENCE TO RELATED APPLICATIONS

This application is a continuation of application Ser. No. 12/994,864, which is a national phase application of PCT/IL2009/000537, which claims the benefit of application No. 61/071,954. The contents of these applications are incorporated herein by reference.

FIELD OF THE INVENTION

The present invention relates to the field of the control of the insertion of flexible needles into a tissue, and especially when the insertion of the needle is observed by ultrasound imaging.

BACKGROUND OF THE INVENTION

Numerous clinical procedures involve needle insertion for diagnostic and therapeutic purposes. Such procedures include biopsies, regional anesthesia, drug delivery, blood sampling, prostate brachytherapy and ablation. These procedures require navigation and accurate placement of the needle tip at an organ, vessel or a lesion. The validity of a diagnosis or the success of a therapeutic treatment is highly dependent on the needle insertion accuracy. For example, in brachytherapy where radioactive seeds are deposited into the tumor by a needle, the effectiveness of the treatment is directly related to the accuracy of the needle placement. The same is obviously true in biopsy where needle misplacement may lead to misdiagnosis.

Physicians often perform the needle insertion procedure free-hand, advancing the needle according to the force feedback from the tool and their 3D perception of the anatomic structure. The performance of such procedures is limited, relying on the physician's training and skills. Although imaging techniques can improve target visibility and needle placement, there still exist causes that contribute to needle misplacement, such as target movement and needle deflection due to tissue deformation. Furthermore, the trajectory may contain obstacles which need to be avoided, thus requiring reiteration of the insertion process. The variability of soft tissue properties may cause unpredictable discrepancy between the planned procedure phase and the treatment phase. It is estimated that of patients who underwent CT-guided needle biopsies, 14% of the tests were valueless due to needle misplacement. Therefore, biopsy procedures are sometimes repeated to ensure adequate sampling, exposing the patient to additional risks and potential complications.

Using a flexible rather than a rigid needle, the above limitations can be largely overcome since the flexible needle tip can be steered to the target, even along a curved trajectory, by maneuvering the needle base. PCT Patent Application No. PCT/IL2007/000682 for "Controlled Steering of a Flexible Needle" (published as WO2007/141784), and the article entitled "Image-guided Robot for Flexible Needle Steering", by D. Glozman and M. Shoham published in IEEE Transactions on Robotics, Vol. 23, No. 3, June 2007, both herein incorporated by reference in their entirety, describe a robotic system for steering a flexible needle in soft tissue under real-time X-Ray fluoroscopic guidance.

This method, used for closed-loop needle insertion, utilizes an algorithm for robotic maneuvering of the needle base, based on a virtual spring model, path planning, needle tip and profile detection, and an iterative estimation of tissue stiffness by analyzing the displacement of the tissue along the length of the needle as a result of forces applied by the needle on the tissue.

A theoretical model for flexible needle steering in soft tissue, based on a virtual spring model, has been presented in the above referenced WO2007/141784. In this model, as illustrated in the schematic drawing of FIG. 1, the needle is held in the robotic base, which applies a lateral force $F_b$ and a moment $M_b$ to the needle. The needle itself is regarded as a linear beam divided into segments, labeled elements 1 . . . i . . . n, in FIG. 1, each of which is subject to lateral spring forces proportional to the virtual spring coefficient and the displacement. Assuming small lateral needle displacements, the tissue response is considered to be linear and the tissue forces are modeled by the lateral virtual springs distributed along the needle. Hence, each segment i, is subjected to point forces, $F_i$, which depend on the local displacement $w_i$, from the initial position, $w_{oi}$, and the tissue stiffness, described by the virtual spring coefficient, $k_i$.

Figure 1:
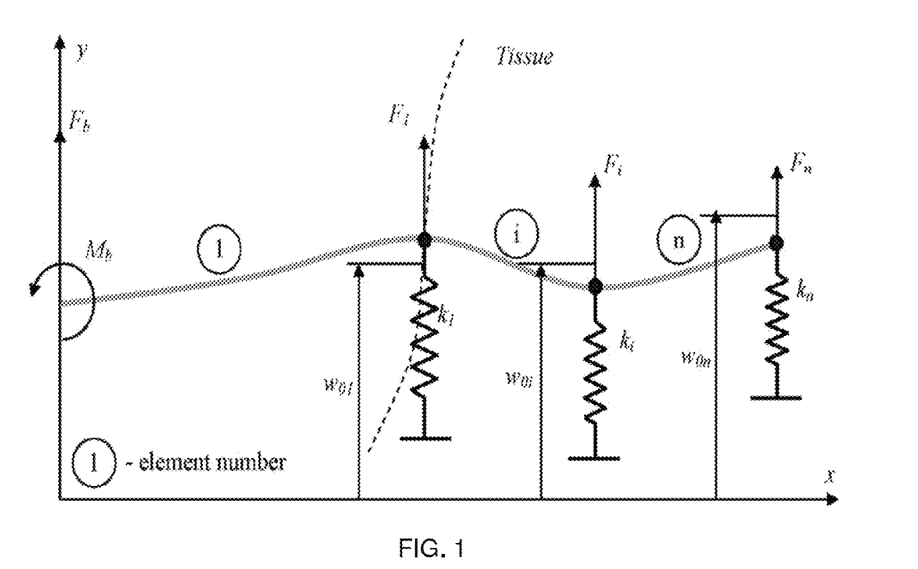
FIG. 1 is a schematic drawing of a theoretical model of a flexible needle, modeled as a linear beam divided into segments, each segment being subject to lateral spring forces.

From the boundary condition at the base, and the second order continuity conditions and spring forces applied between elements, 4×n equations can be derived, described by the following matrix expression:

$$KN=Q \quad (1)$$

where
n is the number of elements,
K is the matrix coefficients of $N_{ij}$,
N is a vector of translation and slope at the edges of each element—$N_{ij}$, where i is the element number and j is the degree of freedom at element i.
Q is a vector including a combination of stiffness coefficients and initial positions of the nodes at the times of their penetration with the needle.

Equation (1) can then be solved to calculate the required orientations and translations of the needle base so that the needle tip will follow the desired path. This is the inverse kinematics problem solution. Among all of the possible paths which avoid the obstacles and do reach the target, the optimal one to use is the path which applies minimal lateral pressure on the tissue, generally related to minimal needle curvature. This is achieved by selecting the tip inclination which minimizes the sum of squares of the virtual spring displacements and slopes.

However, the X-ray fluoroscope tracking described in the prior art involves X-radiation doses to the subject, and incidental scattered radiation exposure to the medical personnel performing the procedure. Additionally, availability of an X-ray system for performing the imaging may be limited, and such equipment is expensive, such that an alternative method of tracking the needle would be desirable.

The disclosures of each of the publications mentioned in this section and in other sections of the specification, are hereby incorporated by reference, each in its entirety.

SUMMARY OF THE INVENTION

This disclosure describes a system and method for steering a flexible needle in a soft tissue under the real time guidance of ultrasound imaging. The use of ultrasound provides advantages over other imaging modalities. The main advantages over the use of X-ray imaging are the absence of radiation hazard, more general availability and lower cost.

However, the interpretation of such an ultrasound image may not be straightforward because of limitations in the visibility of the needle in such imaging. The needle visibility is affected by the angle between the needle and the axis of the ultrasound probe, or more specifically, the direction of the ultrasound imaging. If the ultrasound imaging were to be performed in directions generally sideways to the needle, as is done with X-ray fluoroscopy, (though with ultrasound imaging, this would not usually be a practical method of operation) at least part of the projection of the needle shaft could be seen but the needle tip may not be clearly visible. On the other hand, at imaging directions close to the angle of needle insertion, which are the directions generally used for ultrasound imaging, the needle tip is clearly visible as a bright region, which moves as the needle advances, but the needle itself, is generally difficult to resolve. Thus, the use of US imaging in the commonly used configuration, which enables the position of the tip of the needle to be tracked, this being the ultimate object of the system, does not enable the shaft of the needle to be readily seen.

As a result of this phenomenon, the analysis of the needle insertion process and the resultant robot manipulation as described in the above referenced WO2007/141784 using X-ray fluoroscopy imaging, cannot be performed. In that procedure, every point along the needle's length can generally be seen in the X-ray images and continuously tracked in real time, and knowledge of that path is used for calculating iteratively the stiffness coefficients of the tissue at each point where the needle tip motion has to be determined. Without knowledge of the stiffness coefficients at each insertion increment of the needle, the inverse kinematics equation cannot be solved. At best, an approximate value of the stiffness could be used for the entire insertion, but since the stiffness of the tissue may vary along the needle trajectory, the accuracy of such a procedure would be poor.

The present disclosure presents novel analysis procedures and apparatus which nevertheless enable ultrasound tracking of needle insertion to be achieved, even under such conditions where only the tip of the needle is generally visible. The procedure involves determination of the elastic properties of the tissue at the tip of the needle, by ultrasound elastography measurement of the motion of the tissue in front of the needle tip and in the region immediately around the tip, as it advances into the tissue. Since the stiffness of the tissue is thus measured at the needle tip for every insertion step of the needle, a solution of the inverse kinematic equation, as described hereinabove, can then be readily attained by use of the measured elastic properties of the tissue at the needle tip. This solution enables planning of the forward motion and alignment of the robot for successive iterative steps in inserting the needle so that the needle tip will follow the desired path. Since the tissue stiffness at the tip is known, at least to a first approximation, the solution of the inverse kinematics equation can be achieved more simply than in the above referenced X-ray methodology, where the stiffness of the tissue cannot be measured continually, but is iteratively determined from an initial estimate of the stiffness before insertion, and from the shape of the path of the needle as it progresses. In the present method, the solution of the inverse kinematics equation is also performed iteratively, but using only the observed deviation of the needle tip from its planned path as the feedback parameter for correcting each subsequent insertion step.

Expressing this analytically, it is known that the above referenced matrix expression $$KN=Q \qquad (1)$$

is solved by inverse kinematics to calculate the required orientations and translations of the needle base, so that the needle tip will follow the desired needle trajectory with minimum lateral pressure. However, unlike the above described X-ray imaging procedure, where the stiffness coefficients in Q and K are unknown and therefore have to be estimated iteratively by means of the needle path plotting process described in WO2007/141784, in the ultrasound method of the present disclosure, the stiffness coefficients in Q and K are measured in real time and hence are known at every iterative point of the needle trajectory. As a result, all of the elements of Q and K are known, and the use of ultrasound imaging thus provides a simpler method of finding the inverse kinematic solution to equation (1) than the prior art X-ray imaging procedure. Although this method may be less accurate than taking into consideration any changes in the needle path during insertion, as is done in the X-ray imaging solutions, the technique does enable updating the model according to changes of the tissue stiffness actually measured along the needle trajectory.

Since the position of the tip is known for each insertion step of the needle, the cumulative path of the needle can be determined to a first order approximation by the graphic process of joining these needle tip positions. This path is approximate since it does not take into account any lateral motion of the needle path in proximal sections of the needle as the distal needle tip proceeds further into the tissue. However, it does mean that the entire beam configuration is known in the form of the tissue stiffness at all the incremental points along the length of the known needle path. Although this information is not needed for performing the first order iterative insertion process described in this disclosure, it may be useful in any derivative measurements which may be performed.

Although currently used flexible needles with a smooth surface, are not generally visible in ultrasound imaging procedures performed at angles close to that of the needle entry, techniques may be feasible, particularly using special needle surfaces, which do enable the full length of the needle to become visible under ultrasound imaging. In such a situation, it then becomes possible to measure the elasticity of the tissue along the entire length of the needle, by means of measurements of the movement of the tissue at the lateral sides of the needle as it is inserted, and calculation of the stiffness constants at all those points along the needle's length. Once these stiffness coefficients are known along the length of the needle, together with the needle path, the inverse kinematic solution of equation (1) becomes attainable in closed form, and is readily calculated. This thus represents an alternative method of deriving tissue stiffness for use as a known input parameter to solve the inverse kinematic problem presented in equation (1).

In addition to the use of ultrasound elastography for the determination of the type of tissue being encountered at the tip of the needle, tin order to guide the needle to a predetermined target, this "deep tissue elastography" may be used to determine pathological data about tissue, which would otherwise be difficult to discern from prior art elastography procedures performed by application of external forces at the surface of the tissue.

One example implementation of the systems described in this disclosure involves a system for controlling the insertion of a flexible needle having a tip, into a tissue according to a predetermined trajectory, in which the system comprises:
(i) a robot for maneuvering the needle into the tissue,
(ii) an ultrasound imaging system for ascertaining the position of the tip of the needle,
(iii) a tissue motion analyzer for determining the displacement pattern of the tissue in the region of the tip from ultrasound images, and (iv) a control system to minimize differences between the ascertained position of the tip of the needle and the desired position of the tip according to the predetermined trajectory, wherein the control system is further adapted:

(a) to utilize the displacement pattern of the tissue in the region of the tip to determine the elastic properties of the tissue, (b) to use the elastic properties of the tissue to obtain an inverse kinematic solution to calculate the required motion to be imparted to the needle such that the tip follows the planned trajectory, and (c) to instruct the robot to maneuver the needle into the tissue according to the inverse kinematic solution.

In the above described system, the inverse kinematic solution may be performed on a model of the needle as a flexible beam having a plurality of virtual springs connected laterally thereto to simulate lateral forces exerted by the tissue on the needle, and the lateral forces exerted by the tissue on the needle may be determined from the elastic properties of the tissue derived from the displacement pattern around the needle tip. In such a case, the path of the model of the needle through the tissue may be determined by the influence of the plurality of virtual springs on the needle.

An alternative exemplary system for the insertion of such a flexible needle into a tissue according to a predetermined trajectory, may comprise:

(i) a robot for maneuvering the needle into the tissue, (ii) an ultrasound imaging system for ascertaining the position of the tip of the needle, (iii) a tissue motion analyzer for determining the displacement pattern of the tissue in the region of the tip from ultrasound images, and (iv) a control system controlling the motion of the robot motion to minimize differences between the ascertained position of the tip of the needle and the desired position of the tip according to the predetermined trajectory, wherein the control system may be adapted to utilize a model of the needle as a flexible beam having a plurality of virtual springs connected laterally thereto to simulate lateral forces exerted by the tissue on the needle, and wherein the lateral forces exerted by the tissue on the needle may be determined from elastic properties of the tissue derived from the tissue displacement pattern around the needle tip.

In this described system, the path of the model of the needle through the tissue may be determined by the influence of the plurality of virtual springs on the needle. Additionally, the control system may further utilize an inverse kinematics solution applied to the virtual springs model to calculate the required motion to be imparted to the needle such that the tip follows the planned trajectory.

In any of the above described systems, the predetermined trajectory of the needle may comprise a target for the tip of the needle and at least one region which should be avoided by the needle.

Additionally, the systems may further comprise a force sensor to determine the forces exerted on the needle at its base, in which case the control system also uses the measured forces to determine stiffness properties of the tissue in the vicinity of the needle tip.

Furthermore, in any of the above-described systems, the control system may determine the deviation of the position of the tip determined by image processing of an ultrasound image, from the planned position of the tip according to the predetermined trajectory, and calculates the motion to be applied to the robot to reduce the deviation.

According to further exemplary implementations, the predetermined trajectory may be divided into increments, and the control system may perform the insertion according to these increments in accordance with the real time position of the needle tip obtained from the ultrasound imaging system at each incremental insertion point. Furthermore, the predetermined trajectory may be selected to avoid passage through undesired regions of the tissue.

Additionally, in other implementations of any of the above-described systems, the displacement pattern of the tissue in the region of the tip may be obtained by use of an image processing algorithm, which could conveniently be a bilinear deformable block matching algorithm.

Yet other implementations of the claimed invention described in this disclosure perform a method of utilizing any of the above-described systems.

Still other example implementations involve a method for determining the elastic characteristics of a tissue, comprising:

(i) maneuvering a needle having a tip into the tissue, (ii) generating an ultrasound image of the tip of the needle, (iii) determining the displacement pattern of the tissue around the tip from the ultrasound image, and (iv) utilizing the nature of the displacement pattern to determine the elastic characteristics of the tissue in the region of the tip.

Such a method may further comprise the step of measuring the force applied externally during insertion of the needle, and using the force measurement to determine the elastic characteristics of the tissue in the region of the tip. The nature of the displacement pattern may include at least one of the magnitude and the form of the displacements in the pattern. Additionally, according to these methods, the elastic characteristics of the tissue may be utilized to detect pathological anomalies in the tissue.

Still further exemplary implementations involve a system for determining the elastic characteristics of a tissue, the system comprising:

(i) a needle having a tip, for insertion into the tissue, (ii) a system for generating at least one ultrasound image of the tip of the needle, (iii) a tissue motion analyzer for determining from the at least one ultrasound image, the displacement pattern of the tissue in the region of the tip, and (iv) a tissue analyzer utilizing the nature of the displacement pattern to determine the elastic characteristics of the tissue in the region of the tip.

Such a system may further comprise a force sensor for measuring the insertion force applied to the needle, wherein the force measurement may be used to increase the accuracy of the determining the elastic characteristics of the tissue in the region of the tip. The nature of the displacement pattern may include at least one of the magnitude and the form of the displacements in the pattern. Additionally, the elastic characteristics of the tissue determined using such a system may be utilized to detect pathological anomalies in the tissue.

Another exemplary implementation of the systems described herewithin may further involve a system for controlling the insertion of a flexible needle having a tip, into a tissue according to a predetermined trajectory, the system comprising:

(i) a robot for maneuvering the needle into the tissue, (ii) an ultrasound imaging system for ascertaining the position of the needle, (iii) a tissue motion analyzer for determining the displacement pattern of the tissue along the needle, from ultrasound images, and (iv) a control system to minimize differences between the ascertained position of the tip of the needle and the desired position of the tip according to the predetermined trajectory, wherein the control system may further be adapted:

(a) to utilize the displacement pattern of the tissue along the needle to determine the elastic properties of the tissue, (b) to use the elastic properties of the tissue to obtain an inverse kinematic solution to calculate the required motion to be imparted to the needle such that the tip follows the planned trajectory, and (c) to instruct the robot to maneuver the needle into the tissue according to the inverse kinematic solution.

In such a system, the inverse kinematic solution may be performed on a model of the needle as a flexible beam having a plurality of virtual springs connected laterally thereto to simulate lateral forces exerted by the tissue on the needle, and the lateral forces exerted by the tissue on the needle may be determined from the elastic properties of the tissue derived from the displacement pattern around the needle.

Yet a further exemplary implementation of the systems described herewithin may involve a system for the insertion of a flexible needle having a tip into a tissue, according to a predetermined trajectory, the system comprising:

(i) a robot for maneuvering the needle into the tissue, (ii) an ultrasound imaging system for ascertaining the position of the tip of the needle, (iii) a tissue motion analyzer for determining the displacement pattern of the tissue along the needle from ultrasound images, and (iv) a control system controlling the motion of the robot motion to minimize differences between the ascertained position of the tip of the needle and the desired position of the tip according to the predetermined trajectory, wherein the control system may be adapted to utilize a model of the needle as a flexible beam having a plurality of virtual springs connected laterally thereto to simulate lateral forces exerted by the tissue on the needle, and wherein the lateral forces exerted by the tissue on the needle may be determined from elastic properties of the tissue derived from the displacement pattern along the needle.

In such a system, the path of the model of the needle through the tissue may be determined by the influence of the plurality of virtual springs on the needle. Furthermore, the control system may utilize an inverse kinematics solution applied to the virtual springs model to calculate the required motion to be imparted to the needle such that the tip follows the planned trajectory.

BRIEF DESCRIPTION OF THE DRAWINGS

The present claimed invention will be understood and appreciated more fully from the following detailed description, taken in conjunction with the drawings in which:

FIG. 3A illustrates schematically a needle being inserted into a tissue to show the relative angle between the needle and the ultrasound probe, while

DETAILED DESCRIPTION

Figure 2:
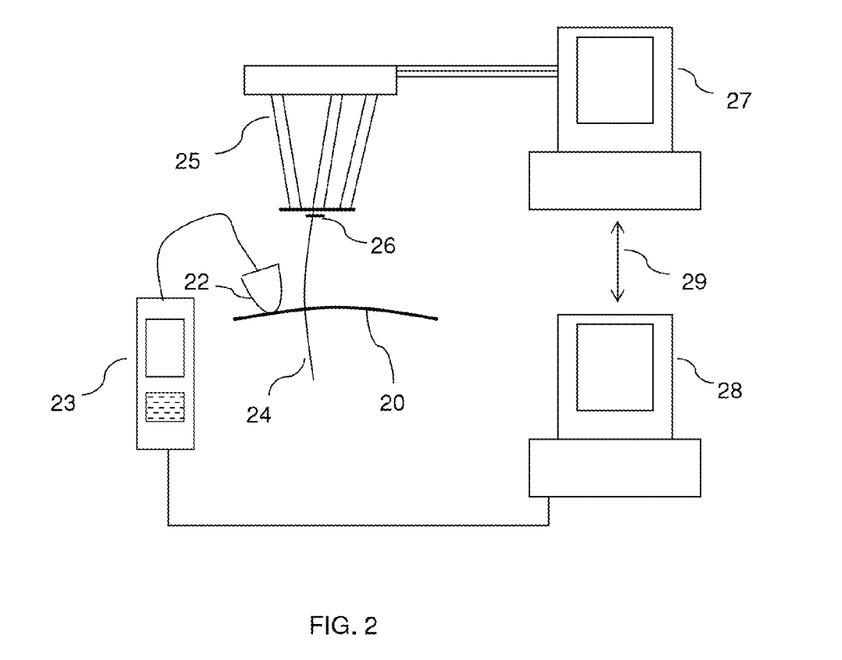
FIG. 2 is a schematic illustration of an exemplary system for performing the ultrasound controlled needle insertion methods described in this application.

Reference is now made to FIG. 2, which is a schematic illustration of an exemplary system for performing the controlled needle insertion methods described in this application. The flexible needle 24 is shown held in the insertion robot 25 and the insertion progress into the subject's tissue 20 is shown being monitored by an ultrasound (US) imaging system, including the ultrasound probe 22 and its control and display system 23. The probe may generally incorporate both the ultrasound transducer and the sensor system for the US energy returned from the needle and tissue. The US control system 23 may generally include the US power supply and the signal processing routines for analyzing the signals received and for generating the US image therefrom.

The robot 25 used for holding the needle 24, and for aligning and propelling it into the patient's tissue 20 may be an RSPR 6DOF parallel robot, such as that described in the article entitled "Image-guided Robot for Flexible Needle Steering", by D. Glozman and M. Shoham, published in IEEE Transactions on Robotics, Vol. 23, No. 3, June 2007. It is to be understood though, that the systems described herein are not meant to be limited to use of a parallel robot structure, but that any serial, parallel or hybrid robotic structure may be used. The robot motion may be controlled by means of its control system 27. The needle may be connected to the robot's moving plate by a 6-DOF force/torque transducer 26, which measures needle insertion forces and torques.

In the exemplary system illustrated in FIG. 2 a separate control system 28 is shown for performing the calculations of the needle motion control algorithm and for running the motion control loop. Its function is to obtain the required needle base coordinates for each insertion step, and to issue commands to the robot so that it moves the needle base to the requested coordinates after calculation of each step of the inverse kinetics equation. The control loop is responsible for receiving incoming data from the US image processing system computer 23, and to generate movement commands based on that data. The raw US data or the US image may be analyzed in order to define the needle tip position, the needle path shape, data related to the tissue elastic characteristics, and insertion force information from the force sensor, for input to the robot control system. This may be performed in the system control computer 28, which may be responsible for the image processing, needle and tissue detections as well as needle control. The system computer 28 commands the motions of the robot via the robot control computer 27. Communication between the two can be provided by a data link 29.

The above described division of control is only one example of how the entire needle insertion system may function, and it is to be understood that the control system may equally well be built around a single computing system, or any suitable alternative division of control and processing functions.

Needle visibility in an ultrasound image depends on several parameters: needle diameter, needle coating, insertion angle and most importantly the alignment of the ultrasound probe plane with the needle, as described in the article entitled "Ultrasound visibility of needles used for regional nerve block: An in vitro study" by I. Schafhalter-Zoppoth et al, published in Reg Anesth Pain Med 2004; Vol. 29, pp. 480-488. The probe alignment may be achieved by using a digitizer, such as the MicroScribe 3DXL digitizer, available from Immersion Products Inc. of San Jose, Calif., calibrated to the robot's coordinate system. The digitizer may then be used to align the ultrasound probe central axis plane to the needle.

Figure 3A:
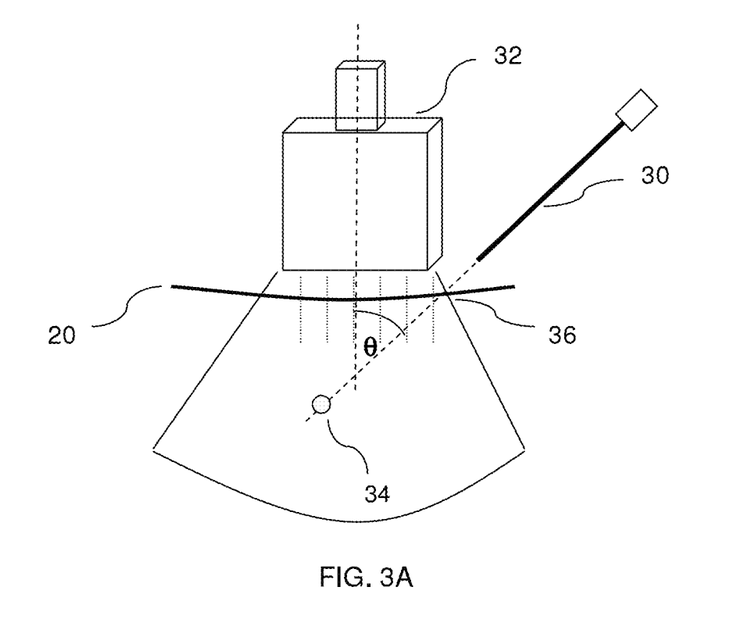
Figure 3B:
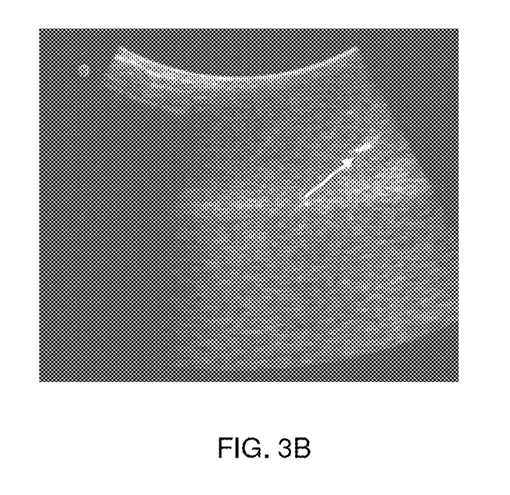
FIG. 3B is an ultrasound images obtained by use of the system of FIG. 2, showing the needle tip appearance as a bright area.

Reference is now made to FIG. 3A, which illustrates schematically a needle 30 being inserted into a tissue 20 at an angle 8 to the direction of ultrasound imaging beam emitted from the US probe 32. The needle is directed from the point of insertion 36, into the tissue 20 towards the target point 34. Experimentation with various angles has shown that at angles close to 90°, the needle shaft may be seen along most of its length, but the needle tip is not clearly visible. However, at angles of 10° to 30°, the needle tip becomes clearly visible in the US image, as a bright area which moves as the needle advances. This is clearly seen in the example of an ultrasound image shown in FIG. 3B, where the position of the needle tip is indicated by the arrow.

Figure 4A:
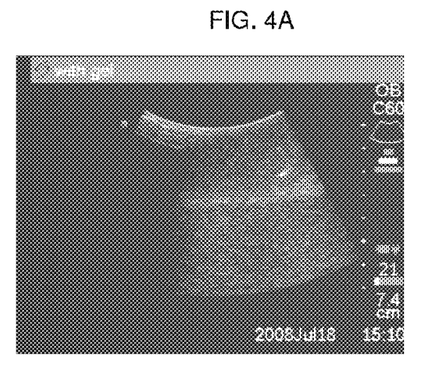
FIGS. 4A to 4C show methods of detecting the needle tip in an ultrasound image such as that shown in FIG. 3B.
Figure 4B:
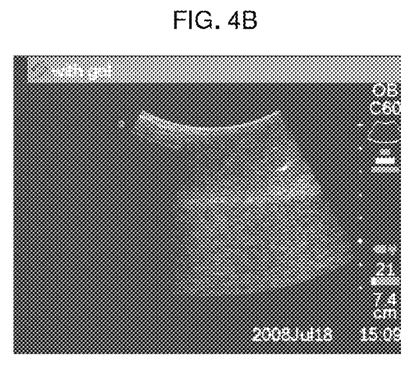
Figure 4C:
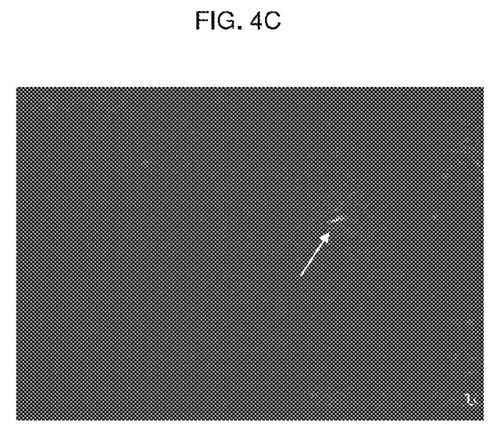

Reference is now made to FIGS. 4A to 4C, which show methods of detecting the needle tip in the ultrasound images. Because of the high level of speckle in the US images, it is not always easy to use image processing directly on the US image to determine the position of the needle tip. The needle tip is seen in FIG. 4A as a bright area. Since, as the needle tip advances, for the close to normal alignment angles used, the main difference from frame to frame is needle tip position, the needle tip can be easily detected by the simple image processing procedure of subtraction of the current frame from a reference frame. FIG. 4B is such a reference frame, taken of the immediately preceding step to that of FIG. 4A, as evidenced by the time stamp on the image. Subtraction of the reference frame of FIG. 4B from the current frame of FIG. 4A results in the image shown in FIG. 4C, where only the needle tip, marked with a white arrow, is seen as a bright area, since it is the only object that changes between the two frames. The image of FIG. 4C is cropped to leave just the tip region, and a threshold is applied to this cropped area. The tip position is considered as the center of the mass of the largest bright area above the threshold level in the difference image. In order to be able to match each pixel from the image coordinate system to the robot coordinate system, image to probe registration is applied, and probe to robot transformation is measured using a digitizer. Using this image-robot registration, the detected needle tip position in the image can be expressed in the robot's coordinate system.

The deviation of the position of the tip from the desired path is then used in the next insertion step, with the magnitude and angle of the needle base insertion being determined by the controller.

Knowing the tissue's stiffness is required for accurate calculation of the inverse kinematics problem. Since there is no a priori knowledge of the tissue properties all the way through from the needle insertion point to the target area, and since using ultrasound, the needle path cannot be used to iteratively estimate the tissue stiffness, a novel method is described in this disclosure for estimating the tissue properties. The method used is based on ultrasound elastography which derives elastic properties of soft tissue from measurement of tissue displacement under the effects of applied forces. Ultrasonic imaging is a common medical imaging technique for producing elastograms.

In prior art ultrasound elastography systems, displacement of the tissue is achieved by applying a compressive force on the tissue surface, and viewing the tissue movement as a result of the superficial force. Such a force causes softer internal tissues to deform more than stiffer ones. This technique is used, for example, for tumor detection by palpable pressure on the tissue. In such procedures, however, the measurement of internal tissue compression is integrated over the whole path, from the tissue surface where the compressive force is applied, to the remote point of interest, and the measurement is therefore of limited accuracy or usefulness.

In contrast to such methods, in the methods of the presently described system, analysis of the ultrasound images is used to determine the local displacement of the tissue caused by the advancement of the needle tip. There are many techniques to estimate tissue motion. According to one approach, tracking the movement of the speckle-pattern in the ultrasound image may be based on the bilinear deformable block matching algorithm, as proposed in the article by A. Basarab, et al, entitled "A method for vector displacement estimation with ultrasound imaging and its application for thyroid nodular disease", published in Medical Image Analysis, Vol. 12, No. 3, June 2008, pp. 259-274, and prepublished on-line in October 2007 as Med. Image Anal. (2007), doi:10.1016/j.media.2007.10.007. However, it is to be understood that such a bilinear deformable block matching algorithm is only one technique by which the image movements may be extracted, and the methods of the present disclosure are not intended to be limited just to this described method.

Since the method described in Basarab et al analyzes the tissue motion due to a compression force applied by the probe on the surface tissue, some modifications are necessary to adapt this method to analyze tissue motion in a region in front of the advancing needle tip. The objective of elastography is to estimate tissue motion between a pair of ultrasound images: a reference frame before deformation, and a comparison frame, after tissue deformation, which is due to the needle movement. In order to achieve this, the reference frame is first divided into regions of interest around defined nodes placed in front of the needle tip. This is shown in the ultrasound image shown in FIG. 5, where the regions of interest are shown as overlapping white rectangles having twice the lateral dimensions as the axial dimension, around the defined nodes, shown as small black crosses. The measured position of the needle tip is shown as a solitary black cross.

Figure 5:
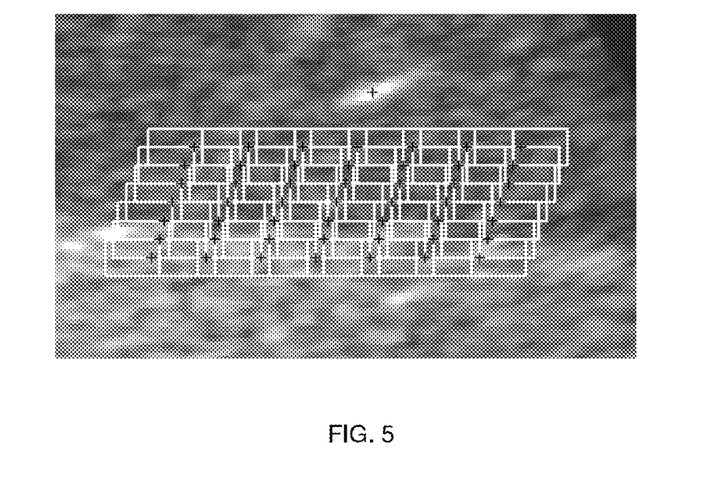
FIG. 5 is an ultrasound image of a reference frame divided into regions of interest around defined nodes placed in front of the needle tip, in order to perform elastography to estimate tissue motion between a pair of ultrasound images.

For a 3.5 MHz frequency US probe, a suitable size is 2.2 mm in the axial direction and 5.6 mm in the lateral direction. Defining overlapping regions of interest increases the accuracy of displacement estimation. The regions of interest may advantageously be arranged with an overlap of 60% in the lateral axis and 50% in the axial axis. The translation of the corners of each ROI is then calculated by a single level block matching algorithm. The block matching criterion is determined by minimizing the sum of squared difference (SSD). In the next step the displacement for all pixels inside the ROI are calculated based on a bilinear model. The unknown bilinear parameters can be found from the calculated displacement of the corners.

Once the complete displacement map has been obtained, then it is analyzed to determine the elastic properties of the tissues in the region surrounding, and in particular, ahead of the needle tip. The displacement field generated around the tip by an applied force depends on the stiffness of the surrounding tissues. Preliminary calibration tests are made to relate the displacement levels obtained to the force applied by the robot to the needle base, when the tangential frictional force along the length of the needle is taken into account. Such preliminary calibration tests may be used to characterize different types of displacement patterns as a function of such parameters as needle size, and the size of the step taken to get to that point. Thus, an inspection of the extent and the distribution of the displacements generated as a function of the force applied enables an estimate of the tissue elasticity to be made. This provides accurate and local data of the elasticity of the tissue at the needle tip. A calibration scale or a look-up table can be generated which enables the estimated stiffness coefficient to be read off from the force applied to the needle, and the tissue motion in front of the needle tip. This tissue stiffness can then be used in the algorithm running in the system controller for determining the next insertion step of the needle insertion, as described hereinabove.

Figure 6:
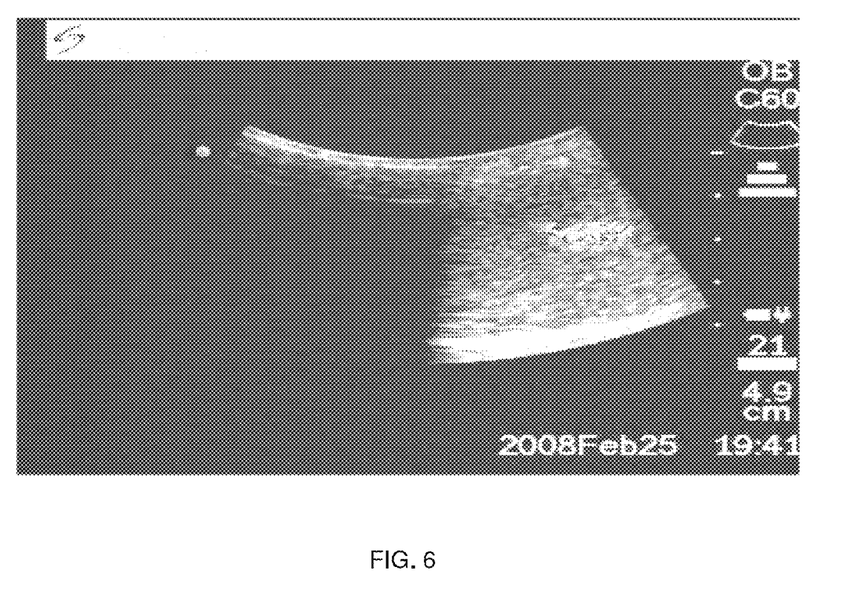
FIG. 6 shows a large area ultrasound image of the region around a needle tip, which is marked in the bright area with a cross.
Figure 7:
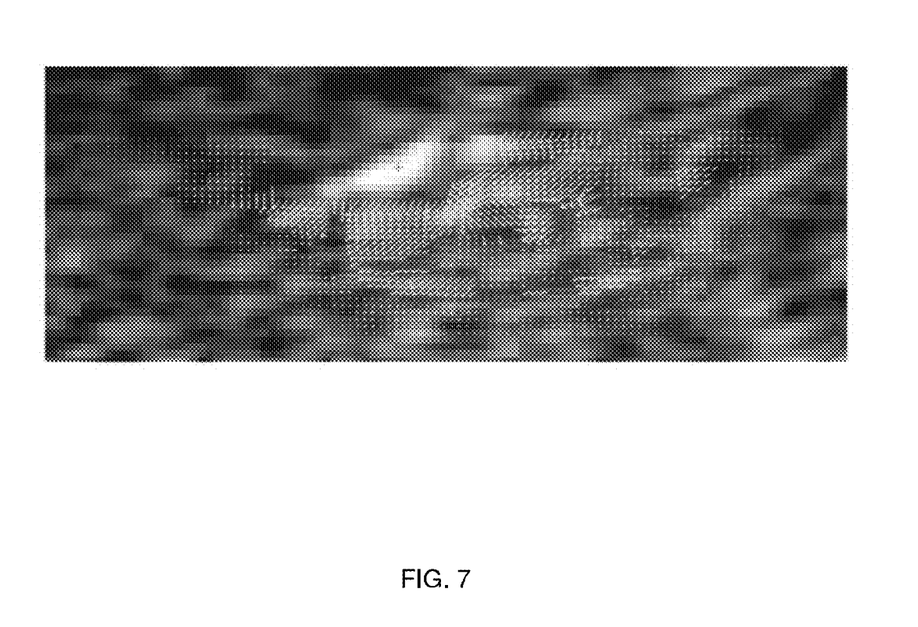
FIG. 7 is an enlarged section of the needle tip area of FIG. 6, showing the tissue displacements marked with small white arrows.

Reference is now made to FIGS. 6 and 7 which illustrate ultrasound scans to demonstrate tissue displacement estimation around the needle tip, for performing the process of tissue stiffness characterization. FIG. 6 is a large area US image of the region around the needle tip, which is marked in the bright area with a cross. FIG. 7 is an enlarged section of the needle tip area of FIG. 6. The individual pixels of the US imaging software can be discerned in FIG. 6. The tissue displacements, as calculated from the ultrasound images using the image processing techniques described in the above referenced article by Basarab et al, are marked with small arrows. Tissues having different stiffness's will show different distributions of arrows. Differences in the motion detected from different types of tissue enable the tissue nature to be determined. Thus, the extent of the region around from the tip, over which tissue motion is detected, provides an indication of the local stiffness of the tissue in that region—the further from the tip the tissue movement is observed, the less the stiffness of the tissue in that region. Additionally, the magnitudes of the movements observed in the tissues around the tip also provides an indication of the local stiffness of the tissue in that region—the larger the movements, the less the stiffness of the tissue in that region.

Figure 8:
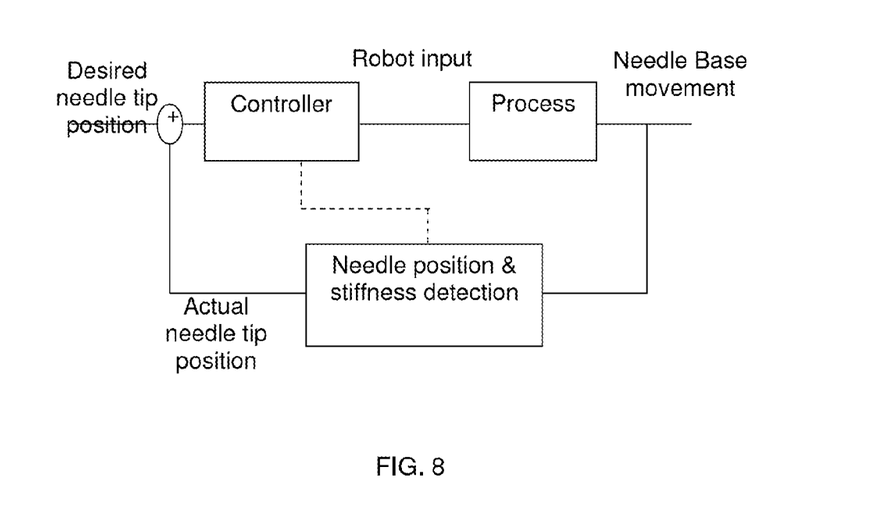
FIG. 8 illustrates schematically an exemplary control loop algorithm used for minimizing the needle tip tracking error during the needle insertion procedure.

Reference is now made to FIG. 8, which illustrates schematically an exemplary control loop algorithm used for minimizing the needle tip tracking error during the needle insertion procedure. The input to the system is the planned needle tip location, excluding its orientation, which will be later optimized by the controller. The actual needle tip location is derived from the ultrasound image and its deviation from the planned position is fed to the controller. The controller calculates for each insertion step, the required needle base movement based on the inverse kinematics of the virtual spring model using the detected tissue stiffness, which is input to the controller by the dashed line. The controller also optimizes needle orientation to minimize lateral tissue pressure. These controller outputs are fed to the robot, which moves the needle base accordingly, inwardly, laterally and angularly, to its next iterative position. The measured tip position minus the desired tip position is the tracking error for that iteration, and is added to the desired tip position as the new input to the controller for the next iteration. The process is continued until the needle tip reaches its planned target. The controller may be a PID controller, but it is to be understood that the invention is not meant to be limited to this mode of control.

A typical needle insertion procedure includes the following steps:
(i) The ultrasound probe is first placed in the needle's plane and a registration procedure is performed.
(ii) The desired target is selected by the user on the ultrasound image, and the needle entry point is determined either by the physician using his judgment, or it can be calculated by the control system computer. The calculation is performed by passing a straight line through the target with the same angle as the angle between the needle orientation and the probe. Then the intersection point of this line with the boundary of the imaging field is translated into the robot coordinate system using image-robot registration and is defined as the entry point.
(iii) Obstacles between the target and the entry point are selected by the user.
(iv) The robot is commanded to move the needle to the entry point and the algorithm for tip detection is applied to detect the initial position of the tip.
(v) Based on the detected initial tip position, the target position and the obstacle (or obstacles) position, a trajectory is calculated by interpolation methods, such as a spline method.
(vi) The controlled needle insertion procedure may then be performed according to the insertion algorithm described above in relation to FIG. 8.

Figure 9:
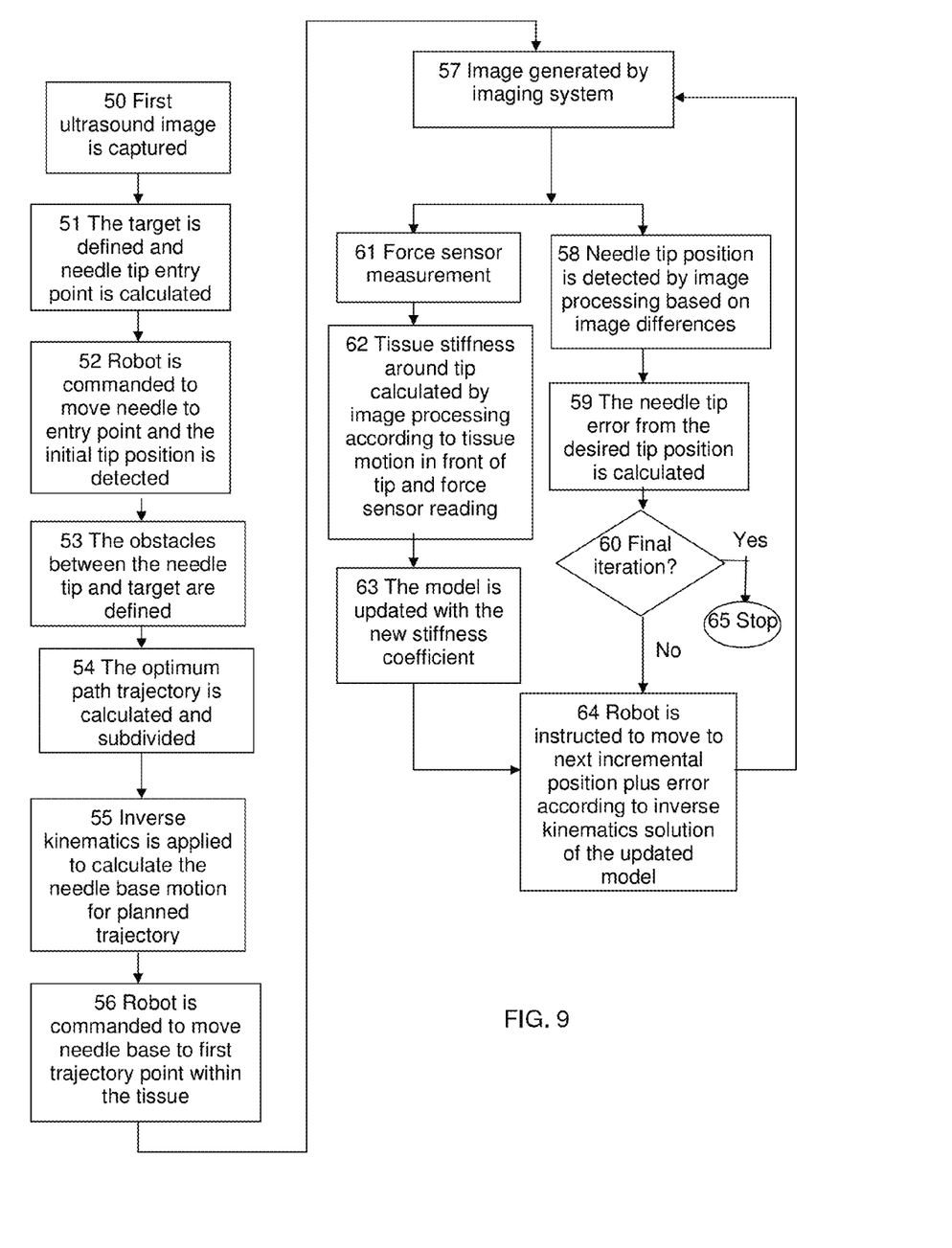
FIG. 9 is a flow chart, showing the steps in a method of insertion of a flexible needle, according to one exemplary procedure described in this disclosure.

Reference is now made to FIG. 9 which is a flow chart, showing the steps in a method of insertion of a flexible needle, according to one exemplary procedure described in this disclosure. The procedure is divided into two parts, steps 50 to 56, which are involved with the preparation for the controlled insertion, and the on-line control algorithm, and steps 57 to 63, which iteratively controls the insertion procedure itself.

In step 50, a first ultrasound image is taken of the region of interest of the subject;

In step 51, the surgeon delineates with the help of a pointing device such as a computer mouse, the target location and a suitable needle tip entry point, whether physician selected or calculated by the control system.

In step 52, the robot is commanded to move the needle to the planned entry point and the initial tip position is detected in the ultrasound image.

In step 53, the surgeon delineates with the help of a pointing device such as a computer mouse any areas between the tip entry point and the target that should be avoided. This step therefore defines the planned trajectory and any constraints thereto.

In step 54, this planned path trajectory is calculated and subdivided into segments for the iterative entry process.

In step 55, a calculation is made, using the inverse kinematics solution described above, to determine the series of needle base motions necessary in order that the tip of the needle follows the predetermined trajectory. The initially assumed values of the tissue stiffness coefficients are used in the first inverse kinematics calculation. Alternatively, after the first puncture of the tissue surface, the force sensor can be used to obtain the stiffness coefficients.

In step 56, the robot receives a command from the control system to commence the insertion procedure itself, by moving the tip to the first trajectory point within the tissue.

In step 57, after completion of the first movement increment, an ultrasound image is taken of the site.

In step 58, the position of the needle tip is determined, by image processing based on the image differences between the previous image—which for the first step was the reference image taken in step 50—and the current image.

In step 59, the error in the position of the needle tip from its desired position, is calculated. This error level is added to the position reached in order to generate the desired position for the next incremental insertion step.

At the same time, in step 61, a force sensor measurement is made, from which the longitudinal force on the needle tip can be determined In step 62, the tissue stiffness around the tip at the first iterative insertion point is calculated by imaging processing, according to the detected tissue motion in the region in front of the tip, and by using the estimated force at the needle tip as calculated from the force sensor readings in step 61. Alternatively, an estimate of the tissue stiffness coefficients is made by using a precalibrated scale of stiffness as a function of tissue movement.

In step 63, the model of the needle trajectory is updated with the newly measured tissue stiffness coefficients, to use in the next iterative step of tip motion.

In step 60, the number of iterations is queried. If the planned number of iterations to the model has been reached, as predetermined in step 54, the insertion is regarded as completed, and the process is stopped at step 65.

If the planned number of iterations has not been reached, a further iteration is performed in step 64. The updated model from step 63 is used in order to calculate, using the inverse kinematic solutions, the robot movement necessary to move the needle tip towards the intended target in the next incremental step, taking into account the optimization for minimal needle deflections, or minimum tissue distortion. To this calculated new target point is also added the error correction from step 59, and the robot is then instructed to move to this combined next desired iteration position.

Once the new incremental movement has been performed, the process flow returns to step 57, where another ultrasound image is obtained, so that the new needle tip position can be ascertained, and the new elastic coefficients of the tissue at that new position can be determined. The process described by steps 58 to 65 then repeats itself, until the final iteration has been performed and the intended target reached.

It is to be understood that the control scheme used in the above-described preferred embodiment of the present invention is only one alternative method, and that the invention is not meant to be limited to use of that scheme, but is meant to include applications using other controllers and other control schemes. Furthermore, although the invention has been described using control in only 2-dimensions, it is to be understood that this is only for purposes of explanation of the system and its method of operation, and that the method and apparatus are equally useable with 3-dimensional controlled motion.

Analyzing the stiffness of the tissue around the needle tip not only provides information of the tissue stiffness from which the maneuvering of the needle base required to follow the desired path is calculated, but it also can be used to estimate the stiffness of the target to ascertain the nature of the tissue reached. The difference in the tissue characteristics could be used to indicate either that a different organ has been reached, or that a tumor has been detected. According to this method, the physician inserts the needle tactically, utilizing, to the best of his abilities, a constant insertion force for the procedure, while viewing the needle tip by means of ultrasound imaging. The displacement pattern of the tissue around the tip is determined from the ultrasound image or images and the nature of the displacement pattern is used to determine the elastic characteristics of the tissue in the region of the tip. In particular, a change in the elastic coefficients observed may indicate the presence of tissue having a pathological anomaly. A system for performing this procedure can be made up of just the needle 24, the ultrasound system 22, 23, and the control system 28, of the system of FIG. 2 hereinabove. According to a more precise procedure, a force sensor 26 may also be used, so that the force used to insert the needle may be measured rather than reliance being placed on the skill of the physician in using a specific or uniform insertion force. There is no need for the robot and its controller, or for the solution of any inverse kinematic equations to perform these methods, though it is to be understood that the method can also be performed using a robot for the insertion process.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method for determining the elastic characteristics of a tissue, comprising:
    maneuvering a needle having a tip into said tissue;
    generating ultrasound images of said tip of said needle;
    using a tissue motion analyzer on said ultrasound images to determine the displacement pattern of said tissue around said tip; and
    utilizing the nature of said displacement pattern to determine the elastic characteristics of said tissue in the region of said tip.

2. A method according to claim 1, further comprising the step of measuring the force applied externally during insertion of the needle, and using said force measurement to determine the elastic characteristics of said tissue.

3. A method according to claim 1 and wherein the nature of said displacement pattern includes at least one of the magnitude and the form of the displacements in said pattern.

4. A method according to claim 1 and wherein said elastic characteristics of said tissue are utilized to detect pathological anomalies in said tissue.

5. A method according to claim 1, where said region of said tip includes a region in front of said tip.

6. A system for determining the elastic characteristics of a tissue, said system comprising:
    a needle having a tip, for insertion into said tissue;
    a tissue motion analyzer for determining from at least two ultrasound images of the region of said tip, the displacement pattern of said tissue in the region of said tip, and
    a tissue analyzer utilizing the nature of said displacement pattern to determine the elastic characteristics of said tissue in the region of said tip.

7. A system according to claim 6, further comprising a force sensor for measuring the insertion force applied to said needle, wherein said force measurement is used to increase the accuracy of said determining the elastic characteristics of said tissue in the region of said tip.

8. A system according to claim 6 and wherein the nature of said displacement pattern includes at least one of the magnitude and the form of the displacements in said pattern.

9. A system according to claim 6 and wherein said elastic characteristics of said tissue are utilized to detect pathological anomalies in said tissue.

10. A system according to claim 6, where said region of said tip includes a region in front of said tip.

* * * * *